(12) United States Patent
Shaninpoor et al.

(10) Patent No.: US 8,123,803 B2
(45) Date of Patent: Feb. 28, 2012

(54) SYSTEM AND DEVICE FOR CORRECTING HYPEROPIA AND PRESBYOPIA

(76) Inventors: Mohsen Shaninpoor, Albuquerque, NM (US); David Soltanpour, New York, NY (US); Parsa Shahinpoor, Albuquerque, NM (US)

( * ) Notice: Subject to any disclaimer, the term of this patent is extended or adjusted under 35 U.S.C. 154(b) by 1020 days.

(21) Appl. No.: 11/626,774

(22) Filed: Jan. 24, 2007

(65) Prior Publication Data
US 2008/0177383 A1   Jul. 24, 2008

(51) Int. Cl.
*A61F 2/14* (2006.01)
(52) U.S. Cl. .......... 623/4.1; 623/5.12; 623/5.15
(58) Field of Classification Search .......... 623/4.1, 623/5.11, 5.12, 5.13, 5.14, 5.16
See application file for complete search history.

(56) References Cited

U.S. PATENT DOCUMENTS

| | | | |
|---|---|---|---|
| 4,961,744 A | 10/1990 | Kilmer | |
| 4,976,719 A * | 12/1990 | Siepser | 606/151 |
| 5,147,284 A | 9/1992 | Fedorov | |
| 5,300,118 A | 4/1994 | Silvestrini | |
| 5,354,331 A | 10/1994 | Schachar | |
| 5,433,714 A * | 7/1995 | Bloomberg | 604/289 |
| 5,465,737 A | 11/1995 | Schachar | |
| 5,489,299 A | 2/1996 | Schachar | |
| 5,503,165 A | 4/1996 | Schachar | |
| 5,529,076 A | 6/1996 | Schachar | |
| 5,722,952 A * | 3/1998 | Schachar | 604/506 |
| 5,766,171 A | 6/1998 | Silvestrini | |
| 5,782,894 A | 7/1998 | Israel | |
| 5,824,086 A | 10/1998 | Silverstrini | |
| 5,888,243 A | 3/1999 | Silverstrini | |
| 5,919,228 A * | 7/1999 | Hennig | 623/5.12 |
| 6,006,756 A | 12/1999 | Shadduck | |
| 6,007,578 A | 12/1999 | Schachar | |
| 6,051,023 A | 4/2000 | Kilmer | |
| 6,192,888 B1 * | 2/2001 | Chandler et al. | 128/846 |
| 6,213,997 B1 | 4/2001 | Hood | |
| 6,214,044 B1 | 4/2001 | Silverstrini | |
| 6,497,700 B1 * | 12/2002 | LaHaye | 606/4 |
| 6,511,508 B1 | 1/2003 | Shahinpoor | |
| 6,849,090 B2 | 2/2005 | Nigam | |
| 6,966,927 B1 | 11/2005 | Silverstrini | |
| 7,018,377 B2 | 3/2006 | Hood | |
| 7,060,094 B2 | 6/2006 | Shahinpoor | |
| 7,090,696 B2 | 8/2006 | Shahinpoor | |
| 7,189,225 B2 * | 3/2007 | Rosen | 606/6 |
| 2002/0055753 A1 * | 5/2002 | Silvestrini | 606/166 |
| 2003/0139808 A1 * | 7/2003 | Shahinpoor et al. | 623/4.1 |

* cited by examiner

*Primary Examiner* — David H Willse
*Assistant Examiner* — Javier Blanco
(74) *Attorney, Agent, or Firm* — V. Gerald Grafe

(57) ABSTRACT

The present invention includes an ophthalmic device and system of mounting for correcting hyperopia and presbyopia. The present invention includes a limbus ring mountable in an encircling relation to a central optic zone of a cornea on a limbus annulus surrounding the cornea. In the limbus ring defines a substantially annular toroid defining a first average diameter that is selectable and has a hydrophilic coating disposed thereon. The inner radius of the limbus ring is selectable such that, upon mounting on the limbus annulus, the limbus ring causes the limbus annulus to contract thereby causing the curvature of the cornea and the eye length to increase. The mounting system of the present invention is adapted to receive a limbus ring and further adapted to selectively place the limbus ring on a limbus annulus.

28 Claims, 12 Drawing Sheets

SYSTEM AND DEVICE FOR CORRECTING HYPEROPIA AND PRESBYOPIA

TECHNICAL FIELD

The present invention relates generally to the field of human and/or mammalian ophthalmic sciences, and more particularly to a system and device for correcting hyperopia and presbyopia in the human and/or mammalian eye.

BACKGROUND AND HISTORY OF THE RELATED ART

There are many refractive errors associated with the human eye. When the focal point of images is formed in front of the retina/macula region due to excess refraction of light rays, the refractive error is called myopia or near-sightedness. When, on the other hand, the focal point of images lie outside the eye behind the retina/macula region due to insufficient refraction of light rays, the refractive error is called either hyperopia or far-sightedness or presbyopia. These problems can be surgically corrected by either changing the eye length or corneal curvatures. In case of presbyopia, as individuals age, the human eye loses its ability to focus on nearby objects. This condition, known as presbyopia, is due to a progressive loss in the elasticity of the lens of the eye, such that the ciliary muscles which normally force the lens, through the action of zonule fibers on the lens capsule, in a rounded shape to accommodate near objects can no longer exert the necessary changes in the lens' shape.

The conventional ophthalmic and/or optometric solution to the problems of myopia, hyperopia, and presbyopia is a prescription of glasses, contact lenses or reading glasses or, for individuals who already require glasses to correct other refractive errors such as myopia or astigmatism, a prescription of bifocal or multifocal glasses.

This century has witnessed a revolution in the surgical treatment of ophthalmic disorders and refractive errors of the human eye. This revolution ranges from corneal implantations, cataract extraction, phacoemulsification of the lens, intraocular lens implantation, glaucoma implants to control the intraocular pressure, radial keratotomy, excimer laser ablation of the cornea, trabeculoplasty, iridotomy, virectomy, and the surgical buckle treatment of retinal detachment. The recent surgical solutions to myopia, hyperopia, and astigmatism have been laser photorefractive keratectomy (PRK). Lasik (laser-assisted in-situ keratomileusis) and RK or radial keratotomy. Modern techniques proposed to correct human eye refractive errors have been corneal implants (Intacs, Silvestrini, et al.) intrastromal corneal ring (ICR, Silvestrini, et al.) and scleral implants (SASI, Schachar, et al.), smart bands (Shahinpoor, et al.) as well as conductive keratoplasty (CK, Mendez, et al.).

The effective focal length of the human eye must be adjusted to keep the image of the object focused as sharply as possible on the retina. This change in effective focal length is known as accommodation and is accomplished in the eye by varying the shape of the crystalline lens. This is necessary for the human eye to have clear vision of objects at different distances. Generally speaking, in the unaccommodated normal vision, the curvature of the lens is such that distant objects are sharply imaged on the retina. In the unaccommodated eye, close objects are not sharply focused on the retina an their images lie behind the retinal surface. In order to visualize a near object clearly, the curvature of the crystalline lens is increased, thereby increasing its refractive power and causing the image of the near object to fall on the retina. The change in shape of the crystalline lens is accomplished by the action of ciliary muscle by which the radial tension in the lens is reduced, according to classical Helmholtz theory of accommodation, and it becomes more convex.

Based on Helmholtz theory, in the unaccommodated human eye the lens and its capsule are suspended on the optical axis behind the pupil by a circular assembly of many radially directed collagenous fibers, the zonules, which are attached at their inner ends to the lens capsule and at their outer ends to the ciliary body, a muscular constricting ring of tissue located just within the outer supporting structure of the eye, the sclera. The ciliary muscle is relaxed in the unaccommodated eye and therefore assumes its largest average diameter. Here by average diameter is meant the half of the maximum plus the minimum diameters possible. According to the Helmholtz classical theory of accommodation, the relatively large average diameter of the ciliary body in this unaccommodated condition, causes a tension on the zonules which in turn pull radially outward on the lens capsule, making it less convex. In this state, the refractive power of the lens is relatively low and the eye is focused for clear vision of distant objects. When the eye is intended to be focused on a near object, the muscles of the ciliary body contract. This contraction causes the ciliary body to move forward and inward, thereby relaxing the outward pull of the zonules on the equator of the lens capsule and reducing the zonular tension on the lens. This allows the elastic capsule of the lens to contract causing an increasing in the sphericity of the lens, resulting in an increase in the optical refraction power of the lens. Recently, Schachar (whose inventions are discussed below) has proposed a radically different theory of accommodation which refutes the Helmholtz theory.

U.S. Pat. No. 5,354,331 to Schachar discloses how presbyopia and hyperopia are treated by a method that increases the amplitude of accommodation by increasing the effective working distance of the ciliary muscle in the presbyopic eye. This is accomplished by expanding the sclera in the region of the ciliary body. A relatively rigid band having a average diameter slightly greater than that of the sclera in that region is sutured to the sclera in the region of the ciliary body. The scleral expansion band comprises anterior and posterior rims and a web extending between the rims, the anterior rim having a smaller average diameter that the posterior rim.

U.S. Pat. No. 5,465,737 to Schachar the teachings are similar to those of the '331 patent, except that by weakening the sclera overlying the ciliary body, by surgical procedures or treatment with enzymes, heat or radiation, whereby intraocular pressure expands the weakened sclera, or by surgical alloplasty. The effective working distance of the ciliary muscle can also be increased by shortening the zonules by application of heat or radiation, by repositioning one or both insertions of the ciliary muscle or by shortening the ciliary muscle. Presbyopia is also arrested according to the invention by inhibiting the continued growth of the crystalline lens by application of heat, radiation or antimitotic drugs to the epithelium of the lens. Primary open angle glaucoma and/or ocular hypertension can be prevented and/or treated by increasing the effective working range of the ciliary muscle according to the invention.

U.S. Pat. Nos. 5,489,299; 5,722,925; 5,503,165; and 5,529,076 to Schachar contain essentially the same ideas as U.S. Pat. Nos. 5,354,331 and 5,465,737 with some improvements such that presbyopia and hyperopia are treated by a method that increases the amplitude of accommodation by increasing the effective working distance of the ciliary muscle in the presbyopic eye. The effective working distance of the ciliary muscle is increased by shortening the zonules by application of heat or radiation, by repositioning one or both insertions of the ciliary muscle or by shortening the ciliary muscle. Presbyopia is also arrested by inhibiting the continued growth of the crystalline lens by application of heat, radiation or antimitotic drugs to the epithelium of the lens. Primary open angle glaucoma and/or ocular hypertension can be prevented and/or treated by increasing the effective working range of the ciliary muscle.

U.S. Pat. No. 6,007,578 to Schachar discloses how presbyopia is treated by implanting within a plurality of elongated pockets formed in the tissue of the sclera of the eye, transverse to a meridian of the eye, a prosthesis having an elongated base member having an inward surface adapted to be placed against the inward wall of the pocket and having a ridge on the inward surface of the base extending along at least a major portion of the major dimension of the base. The combined effect of the implanted prostheses is to exert a radially outward traction on the sclera in the region overlying the ciliary body which expands the sclera in the affected region together with the underlying ciliary body. This restores the effective working distance of the ciliary muscle in the presbyopic eye and thereby increases the amplitude of accommodation. Hyperopia, primary open angle glaucoma and/or ocular hypertension can be treated by increasing the effective working distance of the ciliary muscle.

U.S. Pat. No. 6,006,756 to Shadduck, discloses a system and technique called magnetoresonant induction of an intrastromal implant that is adapted for corneal re-shaping. The technique is utilized to correct mild to high hyperopia and presbyopia by steepening the anterior corneal curvature in a single treatment, or in periodic treatments over the lifetime of the patient. The system comprises a combination of components including (i) at least one implantable magnetoresonant intrastromal segment, and (ii) an oscillating magnetic field generator together with a dosimetry control system including at least one emitter body adapted for positioning proximate to the patient's eye and intrastromal implant. The system can deliver thermal effects to appropriate stromal lamellae by non-contact inductive heating of the implant which in turn contracts or compresses stromal collagen fibrils into a circumferential cinch about an anterior layer of the cornea and steepens the anterior corneal curvature. A dosimetry control system controls the power level and duration of exposure of the oscillating magnetic field(s) and may be combined with intraoperative corneal topography.

U.S. Pat. No. 5,147,284 to Fedorov, et al., teaches a device for restoration of visual functions in cases of affected optic nerve and retina with an electromagnetic field radiator emitting the latter field into the region of the eyeball and an electromagnetic field receiver adapted to interact with the radiator. Both of these exert an electrostimulation effect on the optic nerve and the retina. The electromagnetic field radiator is a source of a pulsed magnetic field and is shaped as an electromagnet provided with an adjuster of a distance between the end of the electromagnet and the electromagnetic field receiver, which is in effect an inductor having lead wires furnished with electrodes whose active surface exceeds 10 mm2. A method for restoration of visual functions in cases of affected optic nerve and retina consists in conducting electrostimulation of the eyeball, for which purpose an inductor is implanted into the orbit on the sclera of the posterior portion of the eyeball in such a manner that one of the inductor electrodes is positioned nearby the external tunic of the optic nerve, while the other electrode is fixed on the sclera in the area of the eyeball equator, whereupon a pulsed magnetic flux is applied remotely to the eyeball portion carrying the inductor, the magnetic field induction being from 0.1 T to 0.25 T, while the pulsed magnetic field is simultaneously brought in synchronism with pulsation of the internal carotid artery.

U.S. Pat. No. 5,782,894 to Israel discloses a device and method for treating presbyopia by which the ciliary muscles of the eyes are electrically stimulated when the internal rectus muscles of the eyes are activated in order to focus the eyes on objects within the near field of vision. The amounts of electrical stimulation can be adjusted according to the individual needs of a patient and are preferably in direct proportion to the amounts of contraction of the internal muscles.

U.S. Pat. No. 4,961,744 to Kilmer, et al, discloses a surgical apparatus for inserting a plastic, split end, adjusting ring into the stroma of the cornea of the eye wherein the adjusting ring includes, as a part thereof, a dissecting head to part the stroma and provide a pathway for the adjusting ring as the ring is rotated. The ends of the adjusting ring are moved to change the shape of the cornea to a desired shape in accordance with the desired visual correction after which the ends of the adjusting ring are fixably joined to maintain the desired shape.

U.S. Pat. No. 5,300,118 to Silvestrini, et al., discloses an intrastromal corneal ring (ICR) that is adjustable in thickness and has an elongated, flexible, preferably transparent or translucent body which forms a circle. The ICR is of a size such that it can be inserted into a human eye and is comprised of a material which is compatible with human ocular tissue. The thickness of the ring can be adjusted so that it is not necessary to stock a plurality of different rings of different sizes to be used in connection with a method of adjusting the shape of the cornea of the eye. A plurality of different embodiments of ICRs are disclosed each of which are adjustable in terms of their thickness. The thickness may be adjusted prior to the insertion of the ICR into the cornea and may not be further adjustable after insertion. However, in accordance with preferred embodiments, the ICR is inserted at a thickness which is believed to be proper and may thereafter be further adjusted in order to precisely define the desired thickness and thereby more precisely adjust the shape of the cornea, and focus the light entering the eye on the retina.

U.S. Pat. No. 5,824,086 to Silvestrini discloses a preformed intrastromal corneal insert. It is made of a physiologically compatible polymer and may be used to adjust corneal curvature and thereby correct vision abnormalities. The insert or segment may also be used to deliver therapeutic or diagnostic agents to the interior of the cornea or of the eye. The insert subtends only a portion of a ring or "arc" encircling the anterior cornea outside of the cornea's field of view. The invention also includes a procedure for inserting the device into the cornea.

U.S. Pat. No. 6,051,023 to Kilmer, et al., discloses a surgical apparatus for inserting a plastic, split end, adjusting ring into the stroma of the cornea of the eye wherein the adjusting ring includes, as a part thereof, a dissecting head to part the stroma and provide a pathway for the adjusting ring as the ring is rotated. The ends of the adjusting ring are moved to change the shape of the cornea to a desired shape in accordance with the desired visual correction after which the ends of the adjusting ring are fixably joined to maintain the desired shape.

U.S. Pat. No. 5,888,243 to Silverstrini discloses an intrastromal corneal ring housing comprising at least one outer layer of a physiologically compatible polymer having a low modulus of elasticity, which polymer may be hydratable and may be hydrophilic. The inner portion of the hybrid intrastromal corneal ring may be hollow or may contain one or more physiologically compatible polymers.

U.S. Pat. No. 5,766,171 to Silvestrini teaches a device and procedure for the correction of optical abnormalities in a human eye. It involves use of an inventive electrosurgical energy probe with specific physical configurations. The process preferably utilizes a high frequency RF electro-desiccation or ablation device. The procedure involves the initial step of forming at least one access site allowing access to the corneal volume behind the Bowman's Layer. It is placed in the anterior surface of the cornea through and ending posterior to the Bowman's layer of the eye. The electrosurgical probe is then introduced into the access site, and depending upon the visual abnormality to be corrected, the probe is activated to adjust the volume of the corneal stromal layers through ablation or desiccation. The shape of the volume desiccated or ablated is dependent upon the aberration to be corrected. In other instances, such as for the treatment of astigmatism, certain smaller sections of the corneal volume may be shrunk. In certain circumstances, the Bowman's layer may be cut to allow the curvature of the cornea to change after the corneal volume adjustment. These relief cuts may be radial, circular, semicircular or any other form appropriate for the option adjustment needed.

U.S. Pat. No. 6,214,044 to Silvestrini teaches an intrastromal corneal ring having comprising at least one outer layer of a physiologically compatible polymer having a low modulus of elasticity, which polymer may be hydratable and may be hydrophilic. The inner portion of the hybrid intrastromal corneal ring may be hollow or may contain one or more physiologically compatible polymers.

U.S. Pat. No. 6,966,927 to Silvestrini presents a hybrid intrastromal corneal ring ("ICR") comprising at least one outer layer of a physiologically compatible polymer having a low modulus of elasticity, which polymer may be hydratable and may be hydrophilic. The inner portion of the ICR may be hollow or may contain one or more physiologically compatible polymers.

U.S. Pat. No. 6,213,997 to Hood and Mendez teaches a thermokeratoplasty system and method for locally heating and reshaping a cornea in a manner that produces a minimal regression of the corneal correction. The system includes a probe that is coupled to a power source which can provide current at a predetermined power, frequency and time duration. The probe has a sharp tip that is inserted into the stroma of the cornea. The tip has an insulated stop that controls the depth of tip penetration. Current flows into the cornea through the probe tip to locally heat and denature the corneal tissue. The denatured tissue causes a subsequent shrinkage of the cornea. A pattern of denatured areas can be created around the cornea to correct the vision of the eye.

U.S. Pat. No. 7,018,377 to Hood and Mendez also teaches a thermokeratoplasty system and method for locally heating and reshaping a cornea in a manner that produces a minimal regression of the corneal correction. The system includes a probe that is coupled to a power source which can provide current at a predetermined power, frequency and time duration. The probe has a sharp tip that is inserted into the stroma of the cornea. The tip has an insulated stop that controls the depth of tip penetration. Current flows into the cornea through the probe tip to locally heat and denature the corneal tissue. The denatured tissue causes a subsequent shrinkage of the cornea. A pattern of denatured areas can be created around the cornea to correct the vision of the eye.

U.S. Pat. No. 6,849,090 to Nigam also describes a biocompatible corneal ring for myopic correction and accommodation for presbyopia. The corneal ring is made from a biocompatible material with a lens body having an inner and outer circular edge. The inner circular edge forms an opening in the lens body. The posterior surface of the lens body has a uniform radius of curvature between the inner and outer circular edges. The anterior surface has two radii of curvatures providing for correction of myopia. The first radius of curvature extends from near the outer circular edge to a junction point before the inner circular edge. The second radius of curvature extends from the junction point and continues to the inner circular edge. The inner and outer circular edges have a thickness of less than about 0.020 mm, but preferably are about 0.010 mm or less.

U.S. Pat. No. 6,511,508 to Shahinpoor, et al., discusses surgical correction of human eye refractive errors such as presbyopia, hyperopia, myopia, and astigmatism by using transcutaneously inductively energized artificial muscle implants to either actively change the axial length and or the anterior curvatures of the eye globe. This brings the retina/macula region to coincide with the focal point. The implants use transcutaneously inductively energized scleral constrictor bands equipped with composite artificial muscle structures. The implants can induce enough accommodation of a few diopters, to correct presbyopia, hyperopia, and myopia on demand. In the preferred embodiment, the implant comprises an active sphinctering smart band to encircle the sclera, preferably implanted under the conjunctiva and under the extraocular muscles to uniformly constrict the eye globe, similar to a scleral buckle band for surgical correction of retinal detachment, to induce active temporary myopia (hyperopia) by increasing (decreasing) the active length of the globe. In another embodiment, multiple and specially designed constrictor bands can be used to enable surgeons to correct astigmatism.

U.S. Pat. No. 7,060,094 to Shahinpoor, et al., teaches surgical correction of presbyopia and hyperopia by a circularly distributed assembly of mini-bridges implanted between the interior surfaces of the ciliary muscle and the exterior surface of the lens capsule, for augmenting the transmission of the contraction force of the ciliary muscle/zonule assembly to the lens capsule. The lens is symmetrically squeezed by mini-bridges acting in concert with the ciliary muscle thus changing the curvature of the lens. The mini-bridges are composite synthetic muscles comprising either passive biocompatible mini-bridges made with polymer gels, silicone polymers or a composite, electromagnetically or mechanically deployable mini-bridges, inflatable balloons or synthetic muscles. The surgical procedure comprises using a ciliary muscle relaxant to stretch the lens/zonules/ciliary muscle assembly. An ultrasonic biomicroscope (UBM) is then used to enable the surgeon to see the area for implantation and the mini-bridges and thus perform endoscopic or incisional surgery to implant the mini-bridges in and around zonular cavities.

U.S. Pat. No. 7,090,696 to Shahinpoor, et al., teaches correction of eye refractive errors like presbyopia, hyperopia, myopia, and astigmatism using either pre-tensioned or transcutaneously energized artificial muscle implants to change the axial length and anterior curvatures of the eye globe by bringing the retina/macula region to coincide with the focal point. The implants are sclera constrictor bands, segments or ribs for inducing accommodation of a few diopters, to correct refractive errors on demand or automatically. The implant comprises an active sphinctering band encircling the sclera, implanted under the conjunctiva and under the extraocular muscles to uniformly constrict the eye globe, to induce active temporary myopia (hyperopia) by increasing (decreasing) the length and curvature of the globe. Multiple and specially designed constrictor bands enable surgeons to correct astigmatism. The artificial muscles comprise materials such as composite magnetic shape memory (MSM), heat shrink, shape-memory alloy-silicone rubber, electroactive ionic polymeric artificial muscles or etectrochemically contractile ionic polymers bands.

SUMMARY OF THE PRESENT INVENTION

Accordingly, the present invention relates to systems and methods of compensating hyperopia and presbyopia by mono vision approach by increasing the curvature of the cornea as well as the length of the eye globe in the direction of optical axis using constricting rings that are either press-fitted, pre-tensioned fitted or heat-shrink-fitted and mounted on the limbus annulus of an eye.

Here by limbus annulus we mean the circular transition region between the cornea and the sclera having typical diameters of about 11-12 mm and typical width of about 1-1.5 mm for human eyes.

Here by heat shrink materials we mean generally thermoplastic materials such as polyolefin, fluoropolymers such as Teflon® (polytetrafluorethylene or PTFE), polyvinylidene fluoride (PVDF) or Kynar, polyvinyl chloride or PVC, polychloroprene (Neoprene) and silicon elastomer or Vitons. Other heat shrink materials such as shape memory materials that shrink when heated to a threshold transition temperature is also included in this invention.

Here by press fitting we mean press sliding a smaller diameter ring with hydrophilic surface coating on the epithelium of the cornea towards the limbus annulus.

Here by hydrophilic coating of the limbus rings means when in the presence of water or body fluids, the hydrophilic polymer adsorbs water molecules to create a water interface at the surface of the plastic ring to reduce sliding friction between the ring and the cornea.

The present invention is described herein with reference to a number of example embodiments. In particular, the present invention includes a system to correct farsightedness or hyperopia in a human and/or mammalian eye by the use of a limbus ring to be mounted on the limbus annulus of an eye by an ophthalmic or optometric physician, for example by being press-fitted, pre-tensioned fitted or heat shrink-fitted. The heat shrink ring can be made inherently electrically conductive and thus can be heated transcutaneously by magnetic inductive heating to shrink to correct tension. By using the limbus ring, one can actively change the corneal curvature as well as the axial length of the eye in order to induce refractive error correction for hyperopia.

In another example embodiment, the present invention teaches a hyperopia (farsightedness) correction method and the associated system in the form of limbus ring with hydrophilic coating mounted on the limbus annulus of an eye by an ophthalmic or optometric physician, for example by being press-fitted, pre-tensioned fitted or heat shrink fitted, in an encircling relation to the central optic zone of the cornea by means of a deployment device. The means for mounting the ring can include ophthalmic glue, medical grade RTV (silicone adhesive), sutures or an encircling set of mini anchors or mini staples. Upon fitting, the endless ring on the limbus causes the limbus annulus of an eye to radially contract, in an encircling relation to the central optic zone of the cornea, causing the curvature of the cornea, as well as the eye length, to increase, thus correcting hyperopia. Placing the ring on the limbus of a single non-dominant eye can also correct presbyopia (mono vision approach).

Example embodiments of the present invention can enable a user to correct hyperopia in a non-invasive and almost non-surgical manner, as well as presbyopia in a non-invasive and almost non-surgical manner. One advantage of the present invention is that the installation of the present invention on a human or mammalian eye does not include irreversible interventions like the present implantable devices such as intacs (stromal tunneling) or laser surgery (corneal ablation or dissection such as RK, PRK and Lasik) or thermokeratoplasty or radio frequency heating and shrinkage of stromal tissues of the cornea such as conductive keratoplasty or CK. Another advantage of the present invention is that it leaves the cornea intact after correction of refractive errors. Another advantage of the present invention is that the operation can take place in an office and no extensive surgical tools are necessary.

Other objects, advantages and novel features, and further scope of applicability of the present invention will be set forth in part in the detailed description of example embodiments to follow read in conjunction with the accompanying drawings.

DETAILED DESCRIPTION OF THE EXAMPLE EMBODIMENTS

The following description of various example embodiments of the invention is not intended to limit the invention to any single preferred embodiment, but rather to enable any person skilled in the ophthalmic arts to make and use the invention.

Example embodiments of the present invention create changes in eye length and corneal curvature to correct hyperopia and presbyopia. The example embodiments further teach a hyperopia (farsightedness) correction method and the associated system in the form of a limbus ring with hydrophilic coating mounted on the limbus annulus of an eye by an ophthalmic or optometric physician, for example by being press-fitted, pre-tensioned fitted or heat shrink fitted, in an encircling relation to the central optic zone of the cornea by means of a deployment device.

The limbus ring of the example embodiments is mountable through the use of ophthalmic glue, medical grade RTV (silicone adhesive), sutures or an encircling set of mini anchors or mini staples. In use, the limbus ring of the example embodiments causes the limbus annulus of an eye to radially contract, in an encircling relation to the central optic zone of the cornea, causing the curvature of the cornea, as well as the eye length, to increase, thus correcting hyperopia. Placing the limbus ring of the example embodiments on the limbus of a single non-dominant eye only can also correct presbyopia in a mono vision correction fashion.

Figure 1A:
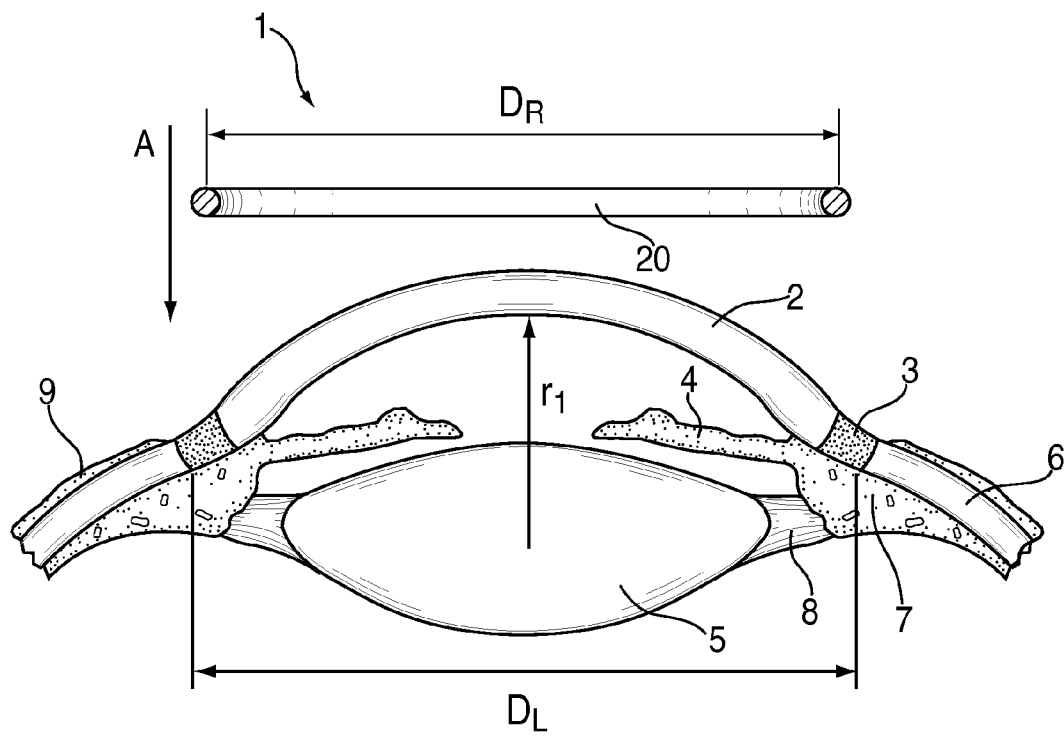
FIG. 1(a) is a cross sectional view of one example embodiment of the present invention in a first position.

FIG. 1(a) is a cross sectional view of one example embodiment of the present invention in a first position. FIG. 1(a) shows an eye globe 1 with transparent cornea region 2 and opaque border region known as the limbus annulus 3. The limbus annulus 3 is located disposed between the cornea 2 and the sclera 6, with an average diameter $D_L$. The eye globe 1 further includes an iris 4, a crystalline lens 5, a group of ciliary muscles 7, a group of lens suspensory ligaments 8 (zonules of Zinn) and conjunctiva or mucus membrane of the eye 9.

In one example embodiment, a limbus ring 20 of average diameter $D_R$, wherein $D_R<D_L$, is shown prior to placement on the limbus annulus 3 along arrow A. The limbus ring 20 is mountable in an encircling relation to a central optic zone of a cornea 2 on the limbus annulus 3 by a physician. The limbus ring 20 can be composed of one or more of a number of materials, including for example a biocompatible plastic similar to the ones used in contact lenses i.e., polymethyl methacrylate or PMMA (Lucite), as well as a silicone or a Teflon elastomers or biocompatible elastic materials surface coated with hydrophilic polymers. Additionally, the limbus ring can be composed of a heat-shrinkable material, such as heat-shrinkable Teflon, a heat-shrinkable fluoropolymer, heat-shrinkable polyolefin, or a heat-shrinkable shape memory material. Additionally, the limbus ring 20 can be composed of a substantially optically translucent material, such that it it will be invisible or does not occlude the passage of light into the eye 1.

Figure 1B:
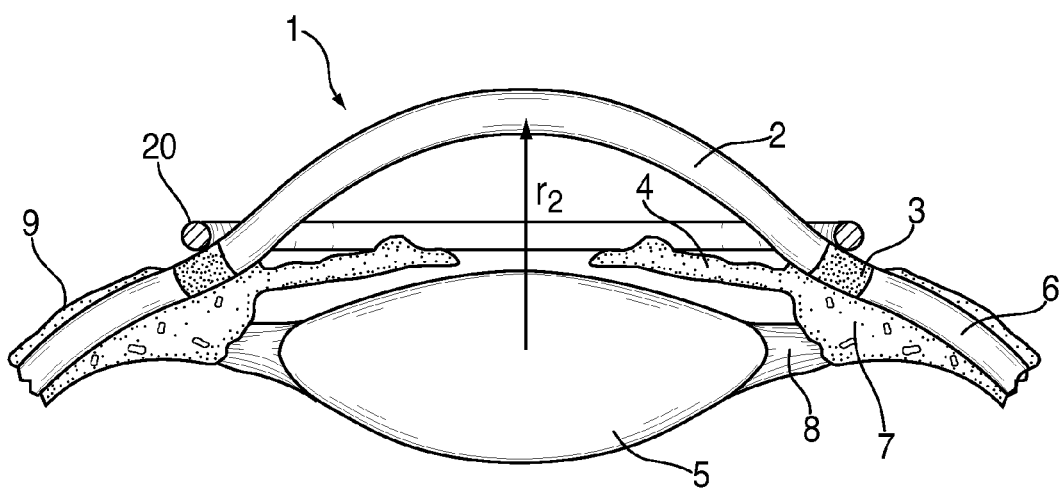
FIG. 1(b) is a cross sectional view of one example embodiment of the present invention in a second position.

FIG. 1(b) is a side view of an example embodiment of the present invention in use. Mounting of the limbus ring 20 of average diameter $D_R$ on the limbus annulus 3 of average diameter $D_L$ where $D_L<D_R$ causes the limbus annulus 3 average diameter to become the same as the limbus ring 10 average diameter and thus cause the corneal curvature ($1/r_1$) to increase to ($1/r_2$) where r2<r1. Accordingly, hyperopic error can be corrected if the correct limbus ring average diameter $D_R$ is selected before placement. This selection is made by the physician either before the limbus ring 20 placement or during placement in the office by observation of the patient. In other example embodiments, the average diameter of the limbus ring 20 can be variable or selectable in response to certain inputs received from the physician. For example, the limbus ring 20 can be composed of a thermally sensitive material that is adapted to decrease the average diameter of the limbus ring 20 in response to a thermal input. In such an example embodiment, the thermally sensitive material can include an electrically conductive material such that the thermal input receivable can include magnetic inductive heating. In another example embodiment, described in detail below, the limbus ring 20 can have a shrink-fit characteristic such that it is adapted to shrink to a specified or predetermined average diameter upon mounting on the limbus annulus 3.

Figure 2A:
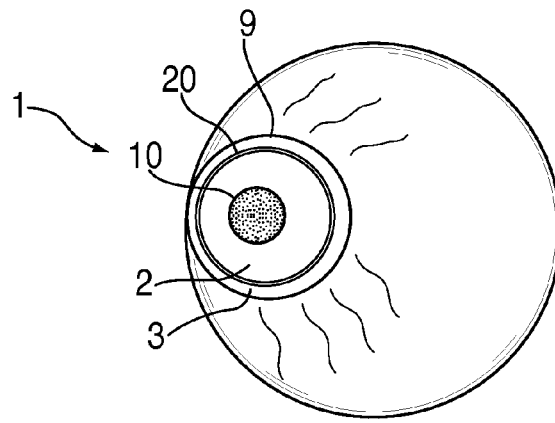
FIG. 2(a) is an isometric view of an eye globe including one example embodiment of the present invention.
Figure 2B:
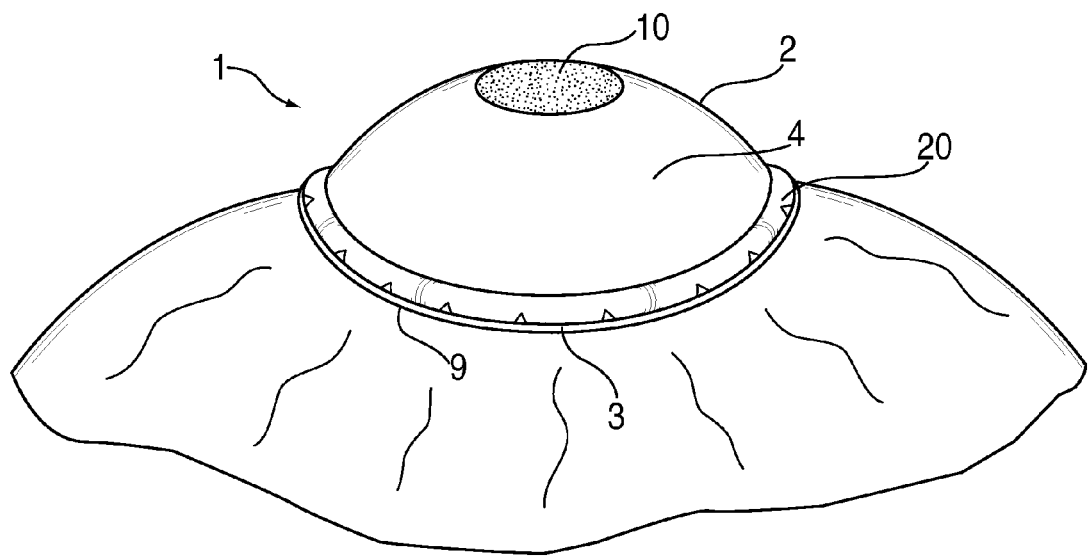
FIG. 2(b) depicts a portion of the eye globe shown in FIG. 2(a).
Figure 2C:
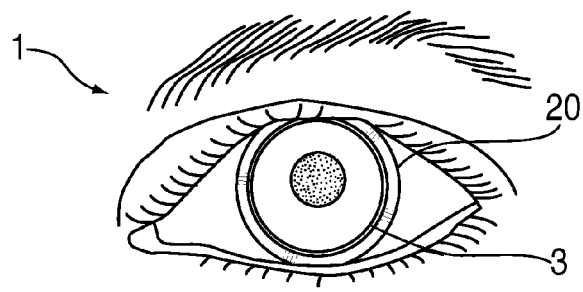
FIG. 2(c) is a view of an eye subsequent to placement of one example embodiment of the present invention.

FIGS. 2(a), 2(b), and 2(c) are representative views of the example embodiment of the present invention described above in use. These figures show an eye globe 1 with a transparent cornea 2, a pupil 10, a sclera globe 11, an opaque limbus annulus region 3, a mucus membrane or conjunctiva border 9 and the constricting limbus ring 20 subsequent to mounting on the limbus annulus 3.

The limbus ring 20 can be composed of one or more of a number of materials, including for example a biocompatible plastic similar to the ones used in contact lenses i.e., polymethyl methacrylate or PMMA (Lucite), as well as a silicone or a Teflon elastomers or biocompatible elastic materials surface coated with hydrophilic polymers. Additionally, the limbus ring 20 can be composed of a substantially optically translucent material, such that it will be invisible or does not occlude the passage of light into the eye 1. The average diameter of the limbus ring 20 can be variable or selectable in response to certain inputs received from the physician. As noted above, the limbus ring 20 can be composed of a thermally sensitive material that is adapted to decrease the average diameter of the limbus ring 20 in response to a thermal input. In such an example embodiment, the thermally sensitive material can include an electrically conductive material such that the thermal input receivable can include magnetic inductive heating. In another example embodiment, described in detail below, the limbus ring 20 can have a shrink-fit characteristic such that is is adapted to shrink to a specified or predetermined average diameter upon mounting on the limbus annulus 3.

Figure 3A:
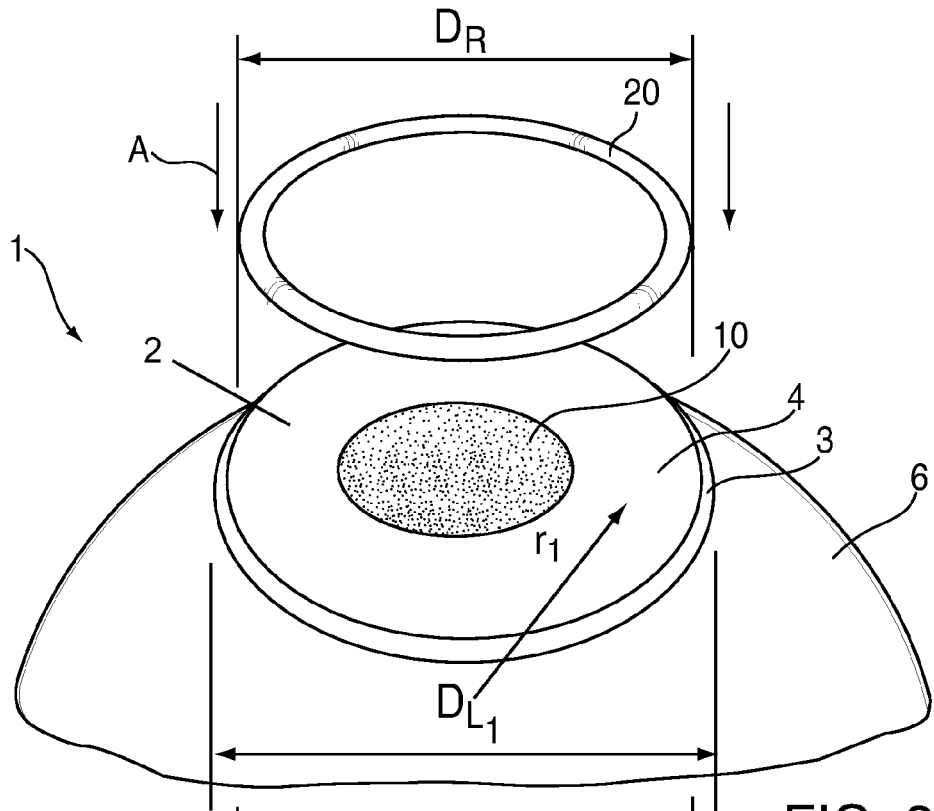
FIG. 3(a) is an isometric view of the present invention depicting a portion of an eye globe receiving an example embodiment of the present invention.
Figure 3B:
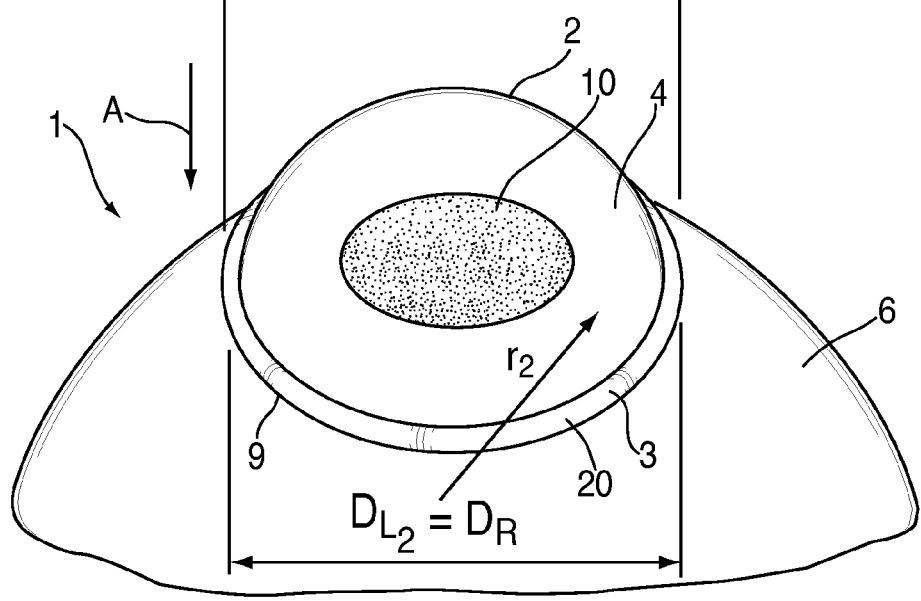
FIG. 3(b) is an isometric view of the present invention depicting a portion of an eye globe upon receipt of an example embodiment of the present invention.

FIGS. 3(a) and 3(b) are further views of the example embodiment of the present invention prior to mounting and subsequent to mounting, respectively. The limbus ring 20 is mountable through the use of a mounting cylinder 30, described in detail below, that permits a physician to slowly advance the limbus ring 20 towards the cornea 2 and to mount it in the limbus annulus region 3 in a substantially symmetrical and encircling manner in relation to the central optic zone of the cornea 2.

The limbus ring 20 of the example embodiments is mountable on the limbus annulus 3 through a number of suitable means, including for example one or more anchors, glue, sutures or staples.

Figure 4:
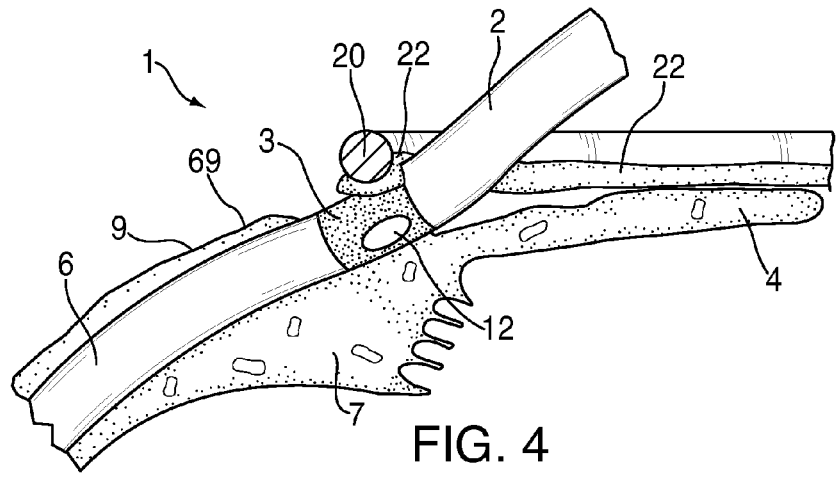
FIG. 4 is partial cross sectional view of an eye upon receipt of an example embodiment of the present invention.
Figure 5:
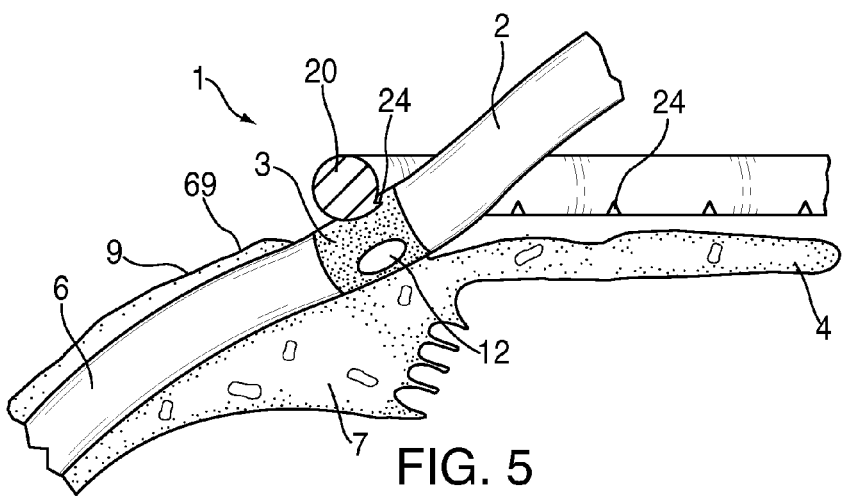
FIG. 5 is partial cross sectional view of an eye upon receipt of another example embodiment of the present invention.
Figure 6:
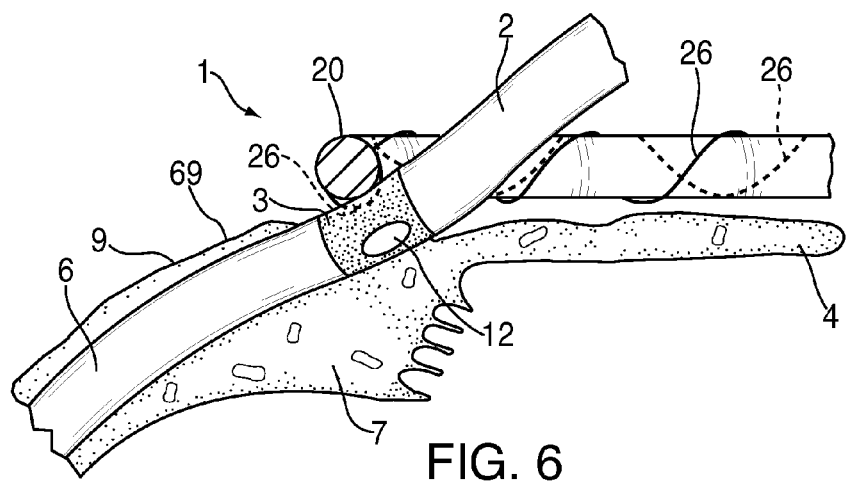
FIG. 6 is partial cross sectional view of an eye upon receipt of another example embodiment of the present invention.

As shown in FIGS. 4, 5 and 6, the limbus ring 20 is mountable on the limbus annulus 3 of the eye 1. In particular, the figures show the limbus annulus 3 region between the cornea 2 and the sclera 6. The iris 4, the Schlemm's canal 12, conjunctiva or mucus membrane of the eye 9, scleral-conjunctival-limbal angular annular groove 69 formed by the anterior border portion of the conjunctiva 9 where it attaches to the sclera 6 and the limbus annulus, ciliary muscles 8 are also depicted to illustrate the placement of the limbus ring 20 with respect thereto. In one example embodiment, shown in FIG. 4, the limbus ring 20 is mountable on the limbus annulus 3 by a medical grade glue 22, such as for example Fibrin or silicone glue RTV. Other adhesives or glues usable in ophthalmic or medical procedures that possess the requisite optical and bio-compatible qualities are also usable according to the example embodiment.

In another example embodiment, the limbus ring 20 is mountable on the limbus annulus 3 through the use of cilia anchors 24 disposable in the cilia of the eye 1. As shown in FIG. 5, the cilia anchors 24 are integrable within the limbus ring 20 itself. Alternatively, the cilia anchors 24 can be non-integral extensions of the limbus ring 20 in the form of cilia composed of a suitable material, such as PMMA, silicone. Teflon or any other biocompatible materials. As shown in FIG. 5, the cilia anchors 24 can be disposed on an interior surface of the limbus ring 20 such that they engage the limbus annulus 3 near the cornea 2, thereby providing an anchoring and constricting force on the limbus ring 20 during wear. The cilia anchors 24 can be distributed uniformly about the limbus ring 20, and they may be of uniform or variable size depending upon the specific application. The cilia anchors 24 can be adapted to anchor into the limbus annulus 3 at any depth through a range of one hundred to three hundred microns, although a typical cilia anchor 24 can anchor at a depth of approximately two hundred microns.

In another example embodiment, the limbus ring 20 is mountable on the limbus annulus 3 through the use of staples, which can be placed by an ophthalmic staple placement means.

In another example embodiment, the limbus ring 20 is mountable on the limbus annulus 3 through the use of sutures 26. As shown in FIG. 6, one or more sutures 26 can be placed around, through, or otherwise in an engaging manner with the limbus ring 20 and the limbus annulus 3 thereby mounting the former on the latter. Any suitable material is usable for the sutures 26, such as those used in ophthalmic surgical procedures that provide the proper optical and bio-compatible characteristics.

Figure 7A:
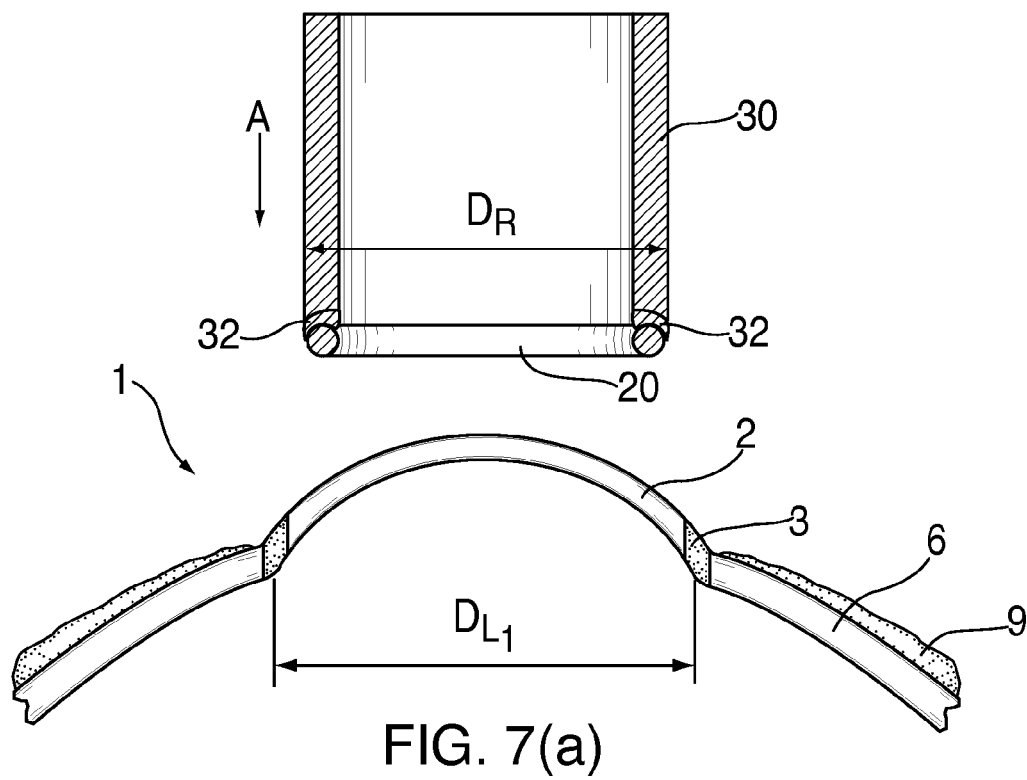
FIG. 7(a) is partial cross sectional view of an eye upon receipt of another example embodiment of the present invention.
Figure 7B:
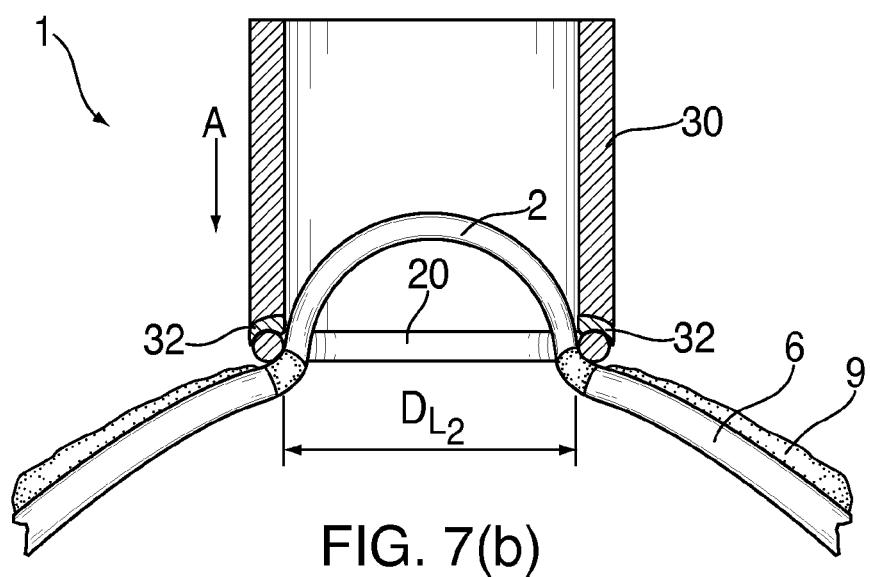
FIG. 7(b) is partial cross sectional view of an eye upon receipt of another example embodiment of the present invention.

The limbus ring 20 is mountable on the limbus annulus 3 through the use of a mounting cylinder 20. As shown in FIGS. 7(a) and 7(b), the mounting cylinder 30 includes a holding tip 32 for selectively holding the limbus ring 20 prior to mounting on the limbus annulus 3. In this example embodiment, the mounting cylinder 30 is adapted to move in a substantially linear manner towards the eye 1 along arrow A. The mounting cylinder 30 is adapted to maintain the average diameter of the limbus ring 20 at an average diameter $D_R < D_L$ before placement on the limbus annulus 3. Subsequent to mounting on the limbus annulus 3, the limbus ring 20 of average diameter $D_R < D_L$ causes the curvature and the length of the eye 1 to increase, thus correcting hyperopia. In addition to the use of glue, anchors, sutures and/or staples, the limbus ring 20 can be press fitted, pre-tensioned fitted, or heat-shrink fitted to the limbus annulus 3. Any combination of mounting mechanisms or methods detailed above is suitable for mounting, such as for example a press fitted limbus ring 20 having cilia anchors and further mounted on the limbus annulus 3 using a glue of the type described above.

Figure 8A:
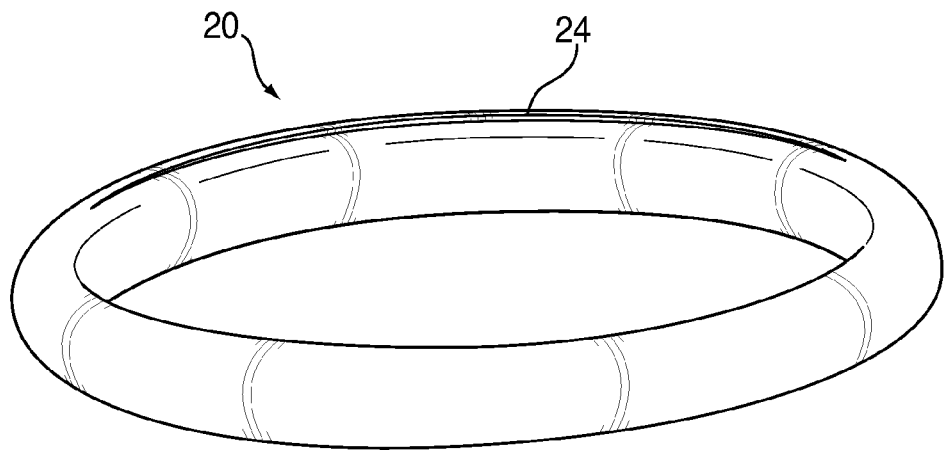
FIG. 8(a) is a wire frame perspective view of a limbus ring in accordance with one example embodiment of the present invention.

As noted above, the limbus ring 20 is mountable on the limbus annulus 3 through a number of means, including for example cilia anchors, glue, sutures, staples or any combination thereof. FIG. 8(a) is a perspective views of a limbus ring 20 having cilia anchors 24 radially disposed on its interior surface, in accordance with one of the example embodiments described above.

Figure 8B:
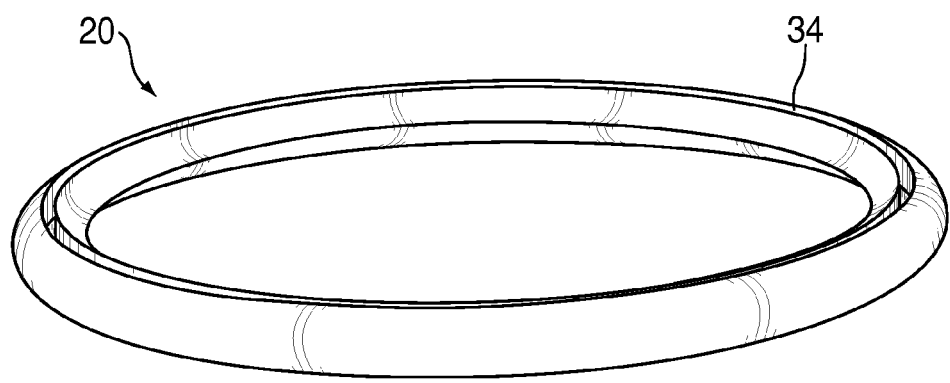
FIG. 8(b) is a wire frame perspective view of a limbus ring in accordance with another example embodiment of the present invention.

In another example embodiment shown in FIG. 8(b), the limbus ring 20 can include a top annular groove (TAG) 34 adapted to engage with the holding tip 32 of the mounting cylinder 30 described herein. As shown herein, the limbus ring 20 defines a substantially annular toroid defining an average diameter. In one example embodiment, the holding tip 32 of the mounting cylinder 30 also defines an average diameter that is greater than that of the limbus ring 20, such that during the mounting process the average diameter of the limbus ring 20 is increased to that of the mounting cylinder 30 for ease of mounting on the limbus annulus 3. Upon removal of the TAG 34 from the mounting cylinder 30, the limbus ring 20 is adapted to return to its nominal average diameter, which is defined above with reference to the curvature of the eye 1.

Figure 8C:
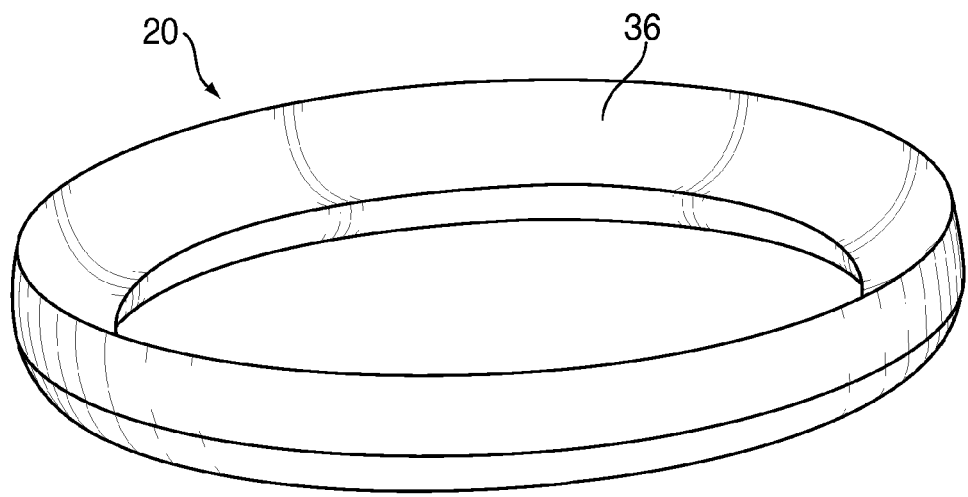
FIG. 8(c) is a wire frame perspective view of a limbus ring in accordance with another example embodiment of the present invention.

In another example embodiment shown in FIG. 8(c), the limbus ring 20 can include a peripheral skirt 36. The peripheral skirt 36 can be disposed about a bottom portion of the limbus ring 20, thereby increasing the surface area of the bottom portion of the limbus ring 20. The peripheral skirt 36 is adapted to engage the limbus annulus 3 through the use of an adhesive or glue of the type described above, and it also can be combined with other example features of the limbus ring 20 such as the cilia anchors 24, the TAG 34, or any combination of mounting methods and means described herein.

Figure 9A:
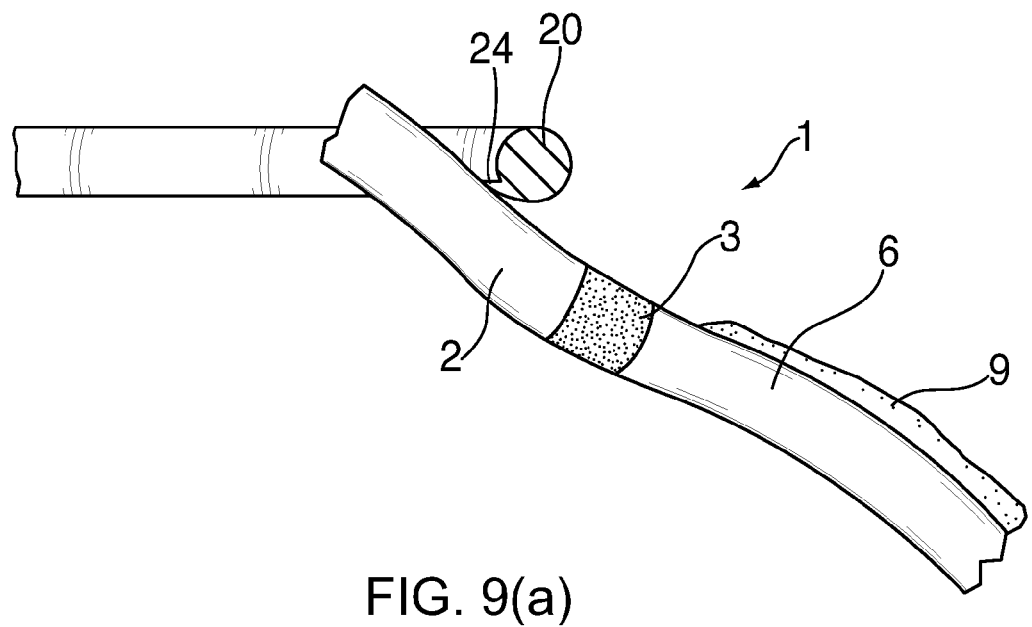
FIG. 9 (a) is a partial cross sectional view of an eye receiving a limbus ring in accordance with one example embodiment of the present invention.
FIG. 9(b) is a partial cross sectional view of an eye receiving a limbus ring in accordance with one example embodiment of the present invention.
Figure 9B:
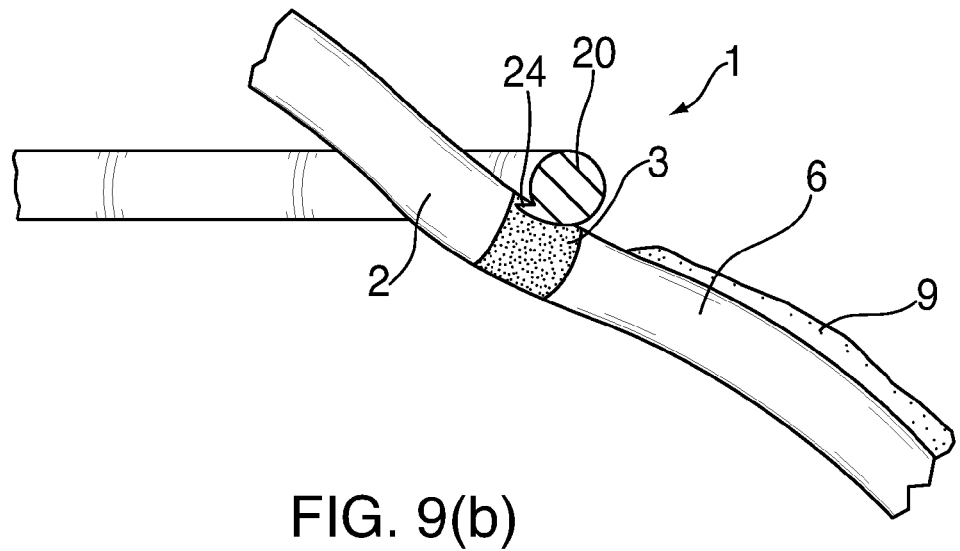

Various mounting methods and means are further depicted in FIGS. 9-11. For example, FIG. 9(a) depicts a portion of the eye 1 with the limbus ring 20 including the cilia anchors 24 pushed and slid on the cornea 2 towards the limbus annulus 3 between the cornea 2 and the sclera 6 with conjunctiva 9. FIG. 9(b) depicts a portion of the eye 1 with the limbus ring 20 including the cilia anchors 24 engaged in the limbus annulus 3 in a secure manner. As noted above, the cilia anchors 24 are typically adapted to penetrate the limbus annulus 3 to a depth of approximately 200 microns.

Figure 10A:
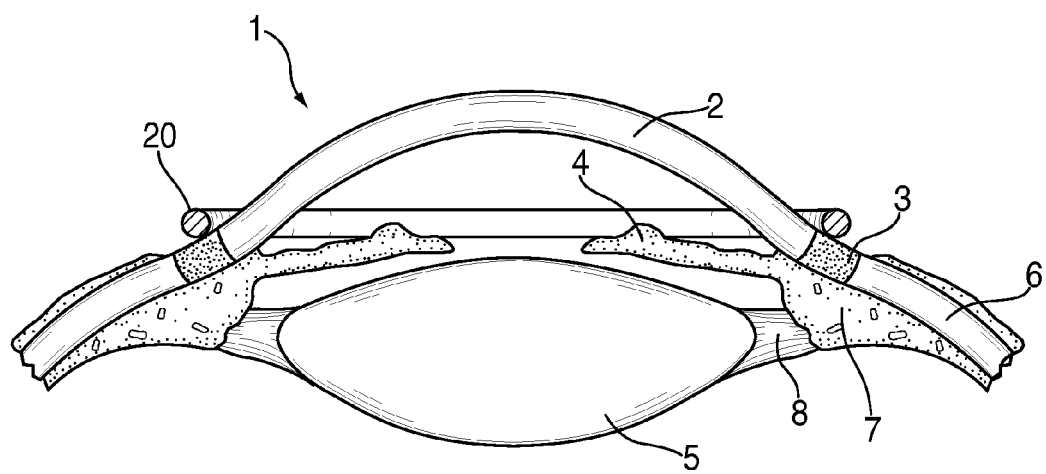
FIG. 10(a) is a partial cross sectional view of an eye receiving a limbus ring in accordance with one example embodiment of the present invention.
Figure 10B:
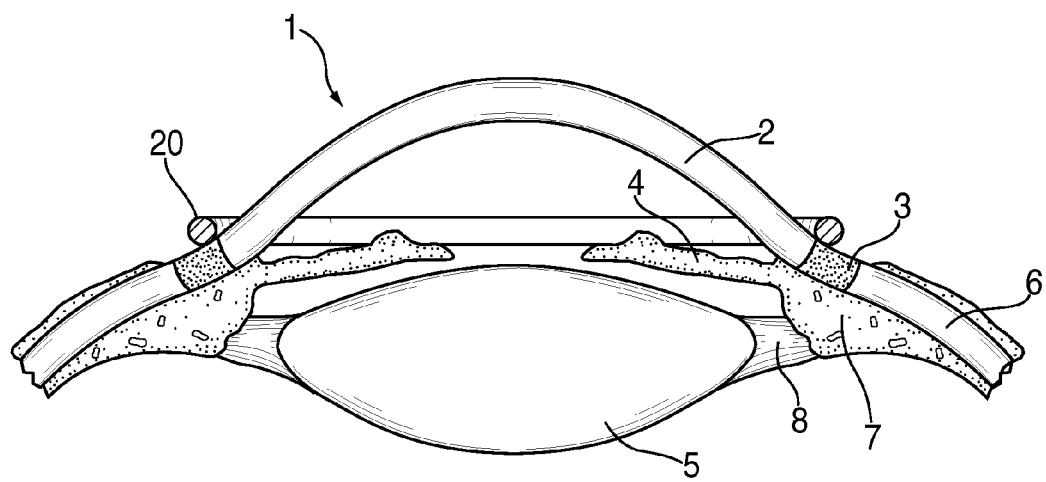
FIG. 10(b) is a partial cross sectional view of an eye receiving a limbus ring in accordance with one example embodiment of the present invention.

FIG. 10(a) depicts a portion of the eye 1 with cornea 2, limbus annulus 3, iris 4, crystalline lens 5, sclera 6, ciliary muscles 7, zonules 8 and a limbus ring 20 mounted on the limbus annulus 3 between the cornea 2 and the sclera 6. The limbus ring 20 shown in FIG. 10(a) is adapted to be heat shrink fittable to the eye 1, such that in response to a thermal input, the diameter of the limbus ring 20 decreases by a predetermined amount as shown in FIG. 10(b). As noted above, the limbus ring 20 can be composed of a thermally sensitive material, including for example an electrically conductive material that is responsive to electromagnetic stimulation. For example, the limbus ring 20 can be heated transcutaneously by magnetic inductive heating to shrink to the correct smaller diameter and tension as determined by the physician.

Figure 10C:
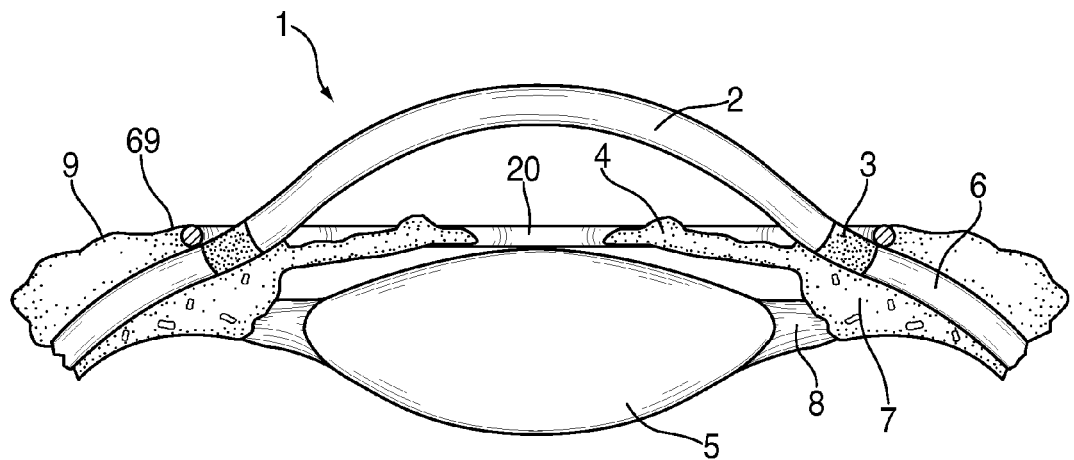
FIG. 10(c) is a partial cross sectional view of an eye receiving a limbus ring in accordance with one example embodiment of the present invention.
Figure 10D:
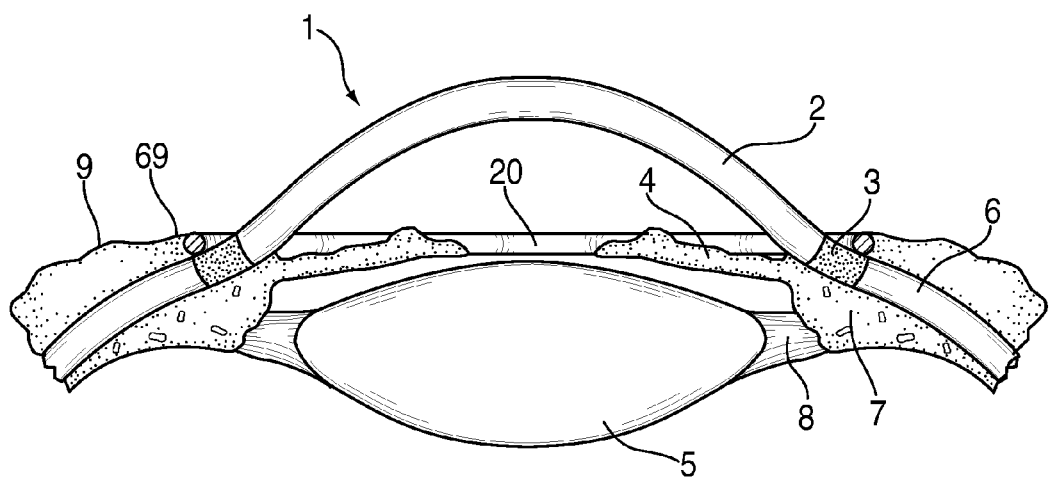
FIG. 10(d) is a partial cross sectional view of an eye receiving a limbus ring in accordance with one example embodiment of the present invention.

FIG. 10(c) depicts a portion of the eye 1 with cornea 2, limbus annulus 3, iris 4, crystalline lens 5, sclera 6, ciliary muscles 7, zonules 8, conjunctiva membrane 9 and a limbus ring 20 mounted under the conjunctive 9 in a scleral-conjunctival-limbal annular angular groove 69 formed by the anterior border portion of the conjunctiva 9 where it attaches to the sclera 6 and the limbus annulus 3. The limbus ring 20 shown in FIG. 10(c) is adapted to be heat shrink fittable to the eye 1, such that in response to a thermal input, the diameter of the limbus ring 20 decreases by a predetermined amount as shown in FIG. 10(d). As noted above, the limbus ring 20 can be composed of a thermally sensitive material, including for example an electrically conductive material that is responsive to electromagnetic stimulation. For example, the limbus ring 20 can be heated transcutaneously by magnetic inductive heating to shrink to the correct smaller diameter and tension as determined by the physician. Surgical means to place the heat-shrinkable limbus ring 20 in the scleral-conjunctival-limbal annular angular groove 69 includes among others, three hundred sixty degree conjunctival peritomy and the placement of the ring 20 in the groove 96 and then suturing back or gluing back the conjunctiva to the limbus annulus 3 by standard sutures or ophthalmological glue such as Fibrin.

Figure 11A:
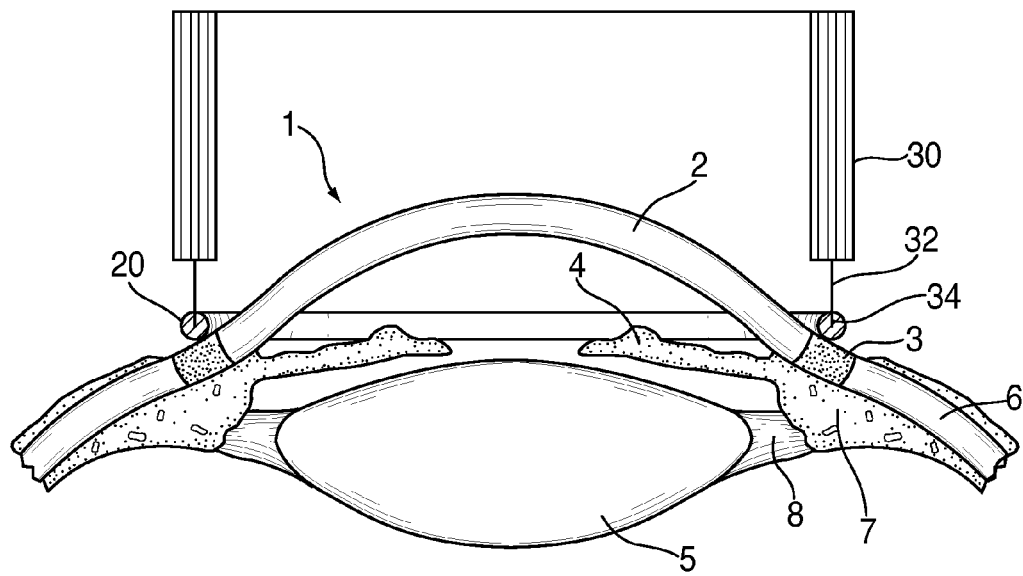
FIG. 11(a) is a partial cross sectional view of an eye receiving a limbus ring in accordance with one example embodiment of the present invention.

FIG. 11(a) depicts a portion of the eye 1 with cornea 2, limbus annulus 3, iris 4, crystalline lens 5, sclera 6, ciliary muscles 7, zonules 8 and a limbus ring 20. As noted above, the limbus ring 20 can be pre-tensioned such that it automatically constructs to its average diameter upon mounting on the limbus annulus 3. As shown in FIG. 11(a), the limbus ring 20 includes a TAG 34 for connecting it to the holding tip 32 of the mounting cylinder 30. Upon removal of the TAG 34 of the limbus ring 20 from the holding tip 32, the limbus ring constricts to its predetermined average diameter as shown in FIG. 11(b).

Figure 11B:
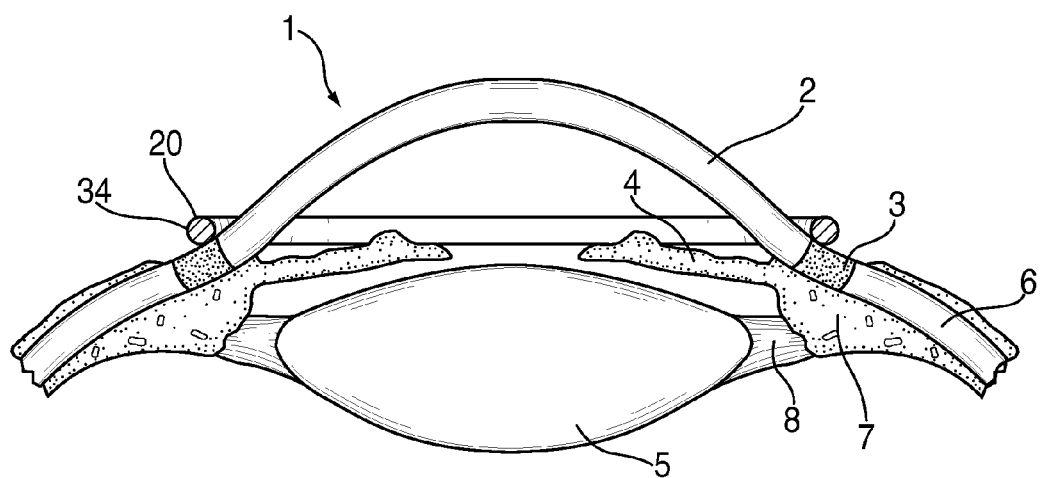
FIG. 11(b) is a partial cross sectional view of an eye receiving a limbus ring in accordance with one example embodiment of the present invention.

FIG. 11(b) depicts a portion of the eye 1 with cornea 2, limbus annulus 3, iris 4, crystalline lens 5, sclera 6, ciliary muscles 7, zonules 8 and pre-tensioned limbus ring 9 mounted on the limbus annulus 3 between the cornea 2 and the sclera 6 after the tip of the mounting cylinder 11 in the limbus ring top annular groove (TAG) 12 is removed from the limbus ring to cause it to shrink to a smaller diameter.

Figure 12A:
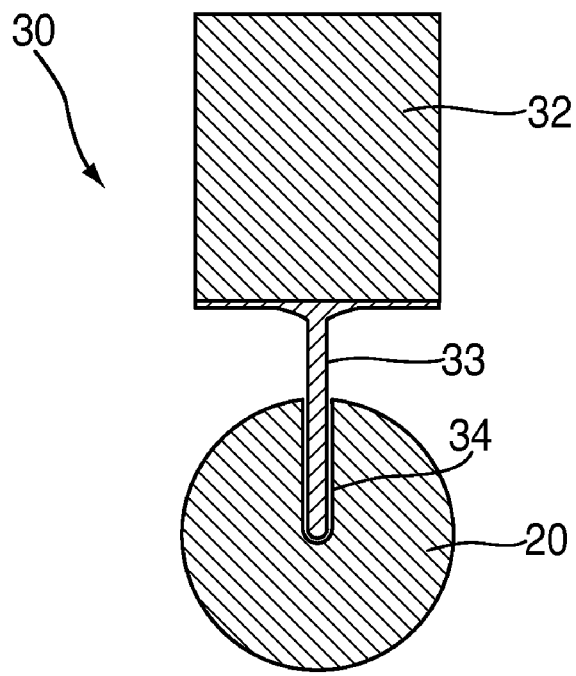
FIG. 12(a) is a partial cross sectional view of one example device for holding a limbus ring in accordance with one example embodiment of the present invention.

FIG. 12(a) depicts a portion of an example mounting cylinder 30 adapted to engage the TAG 34 of the limbus ring 20. The mounting cylinder 30 includes the holding tip 32 which further includes a cylinder edge 33, which is adapted to selectively mate with the TAG 34 of the limbus ring 20. The mounting cylinder 30, as described above, is adapted to engage the limbus ring 20 until it is mounted on the limbus annulus and either glued, anchored, stapled and/or sutured before the mounting cylinder 30 is removed and the limbus ring 20 is left by itself on the limbus annulus 3.

Figure 12B:
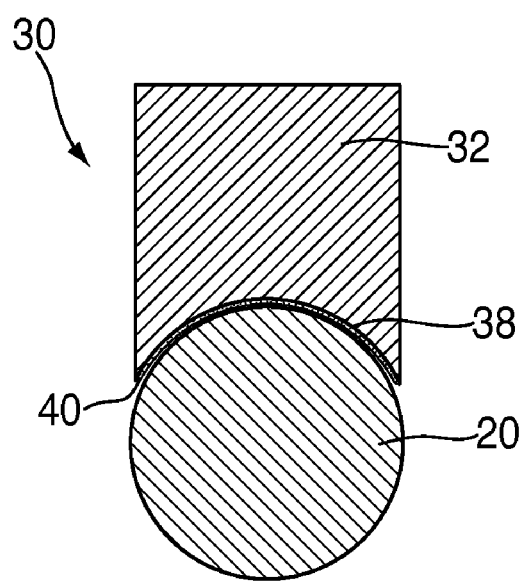
FIG. 12(b) is a partial cross sectional view of another example device for holding a limbus ring in accordance with another example embodiment of the present invention.

FIG. 12(b) depicts a portion of another example mounting cylinder 30 adapted to selectively engage the limbus ring 20 during mounting. The mounting cylinder 30 includes the holding tip 32, which further defines a groove 38 defining a substantially half-cylindrical cross-section for receiving the limbus ring 20. The surface of the groove 38 can include an adhesive 40 that is adapted to selectively hold the limbus ring 20 during the mounting procedure, and thereafter it is easily detachable once the limbus ring 20 is mounted either by gluing, anchoring, stapling and/or suturing it to the limbus annulus 3.

Another example embodiment of the present invention includes a mounting system alignable along an optical axis including a central optic zone of a cornea. The mounting system of the example embodiment is adapted to receive a limbus ring and further adapted to selectively place the limbus ring on a limbus annulus. As described below, the mounting system can be movable in a direction substantially parallel to the optical axis and rotatable in a direction substantially orthogonal to the optical axis.

Figure 13:
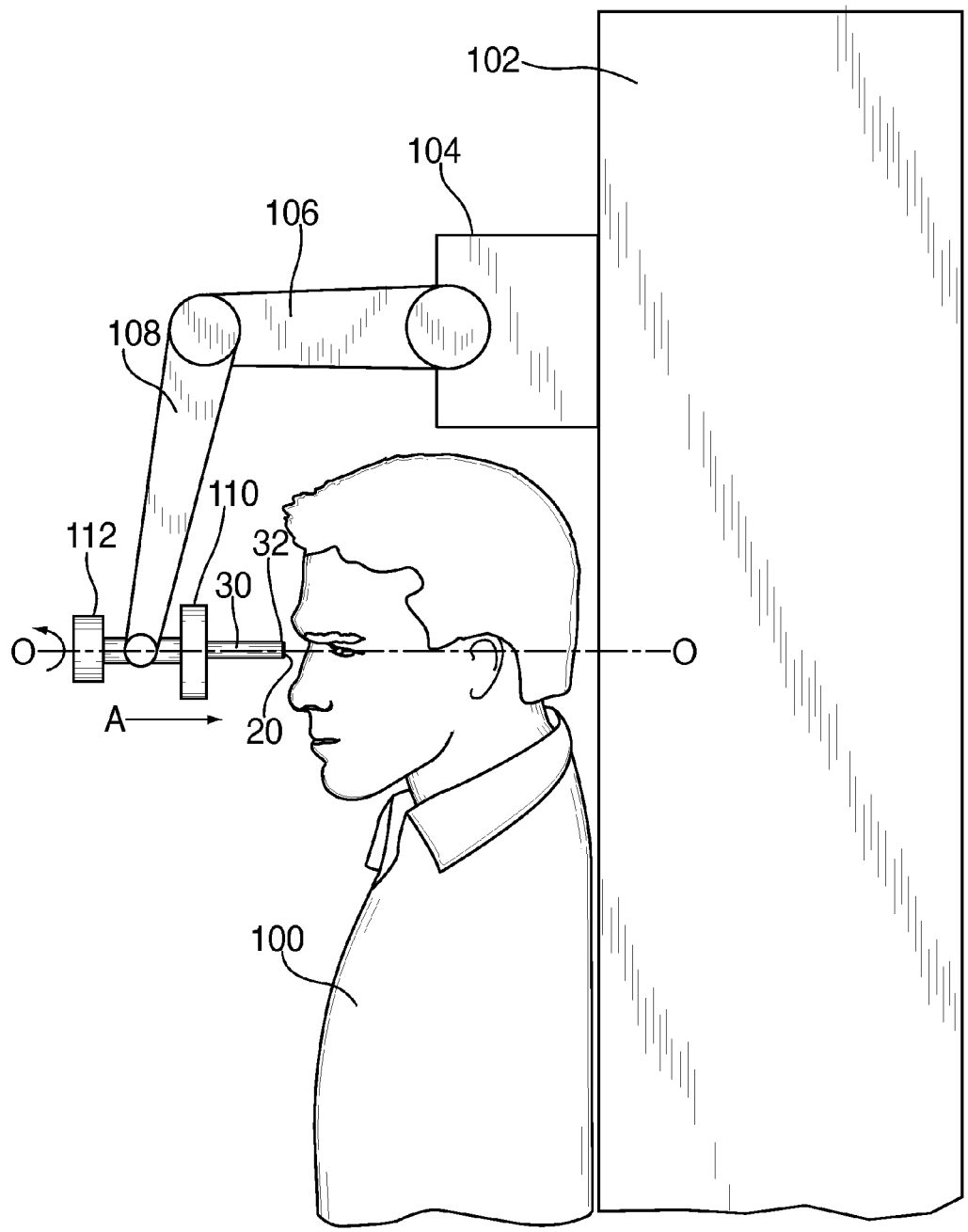
FIG. 13 is a partial view of a system for the placement of a limbus ring during a procedure in accordance with one example embodiment of the present invention.

FIG. 13 is a schematic diagram of a mounting system in accordance with the example embodiment, depicts the placement of the limbus ring 20 on a patient 100. As shown in the example embodiment, the patient 100 can be placed on a platform 102 that is connected to or selectively connected to a mounting fixture 104. In use, the patient 100 will typically be oriented on his or her back with one or both eyes open and dilated. The example system further includes one ore more adjustable linkage 106, 108 that are attachable to both the mounting fixture 104 and a guide bushing 110.

The example system further includes an advancing device 112, which cooperates with the guide bushing to move the mounting cylinder 30 along the optical axis O-O in the direction of arrow A. Additionally, the advancing device 112 can be adapted to rotate the mounting cylinder 30 about the optical axis O-O, thereby giving a user an additional degree of freedom with respect to placement of the limbus ring 20. The advancing device 112 can include mechanical, electrical, electromechanical, optical or any other suitable combination of means or mechanisms for advancing the mounting cylinder 30 during the mounting procedure. For example, the guide bushing 110 can include internal precision threads and an advancing screw (not shown) to enable a physician to slowly advance the limbus ring 20 attached to the mounting cylinder 30 along arrow A and about the central optical axis O-O. The mounting cylinder 30 can include a holding tip 32 adapted to engage the limbus ring 20 through any of the methods or means described above, including for example through a TAG 34 disposed on the limbus ring 20 or through engagement on the groove 38 described above.

As a person skilled in the ophthalmic arts will recognize from the previous detailed description and from the figures, modifications and changes can be made to the preferred embodiment of the invention without departing from the scope of this invention defined in the following claims.

We claim:

1. An ophthalmic device comprising a single limbus ring mountable for periods of longer than one day without causing damage to the eye, and mountable without requiring surgical incision and without restricting blood flow to an extent that is harmful to the eye when maintained for a period longer than one day, in an encircling relation to a central optic zone of a cornea on a limbus annulus surrounding the cornea, the limbus ring having a cross-section having a portion that is curved to correspond with the shape of the limbus and having mounting features that engage the limbus to retain the ring in position on the eye without force external to the limbus ring; the limbus ring defining a first average diameter and wherein the limbus annulus defines a second average diameter, wherein the first average diameter is selectable such that the first average diameter is less than the second average diameter; the limbus ring having an inner radius that is selectable such that, upon mounting on the limbus annulus, the limbus ring causes the limbus annulus to contract thereby causing the curvature of the cornea and the eye length to increase by an amount selected to cause objects in view to be sharply focused on the retina.

2. A device as in claim 1 wherein the limbus ring comprises polymethyl methacrylate.

3. A device as in claim 1 wherein the limbus ring comprises a silicone elastomer.

4. A device as in claim 1 wherein the limbus ring comprises a heat-shrinkable Teflon.

5. A device as in claim 1 wherein the limbus ring comprises a heat-shrinkable fluoropolymer.

6. A device as in claim 1 wherein the limbus ring comprises a biocompatible elastic material.

7. A device as in claim 1 wherein the limbus ring comprises a heat-shrinkable material.

8. A device as in claim 1 wherein the limbus ring comprises heat-shrinkable polyolefin.

9. A device as in claim 1 wherein the limbus ring comprises a heat-shrinkable shape memory material.

10. A device as in claim 1 wherein the limbus ring is substantially optically translucent.

11. A device as in claim 1 wherein the limbus ring comprises a thermally sensitive material that is adapted to decrease the first average diameter in response to a thermal input.

12. A device as in claim 11 wherein the thermally sensitive material includes an electrically conductive material and wherein the electrically conductive material heats responsive to magnetic inductive heating.

13. A device as in claim 1 wherein the limbus ring comprises a radially distributed cilia anchor adapted to retain the limbus ring in the limbus annulus surrounding the cornea.

14. A device as in claim 13 wherein the cilia anchor is disposed on an interior surface of the limbus ring.

15. A device as in claim 13 wherein the cilia anchor is adapted to anchor into the limbus annulus at a depth of approximately 200 microns.

16. A device as in claim 1 wherein the limbus ring further comprises a top annular groove adapted to receive a mounting cylinder having a third average diameter, and wherein the third average diameter is greater than the first average diameter.

17. A device as in claim 16 wherein, upon removal of the top annular groove of the limbus ring from the mounting cylinder, the limbus ring contracts to the first average diameter.

18. A device as in claim 1 wherein the limbus ring further comprises a peripheral skirt disposed about a bottom portion of the limbus ring thereby increasing the surface area of the bottom portion of the limbus ring.

19. A device as in claim 1 wherein the limbus ring is mountable on the limbus annulus using one of anchors, glue, sutures, or staples.

20. A device as in claim 1 wherein the limbus ring is press fittable to the limbus annulus.

21. A device as in claim 1 wherein the limbus ring is pre-tensioned fittable to the limbus annulus.

22. A device as in claim 1 wherein the limbus ring is heat shrink fittable to the limbus annulus.

23. A device as in claim 1 wherein the limbus ring is heat shrink fittable in the scleral-conjunctival limbal annular angular groove.

24. A system for aiding in the correction of hyperopia and presbyopia comprising a limbus ring as in claim 1 and a mounting system alignable along an optical axis including a central optic zone of a cornea, the mounting system adapted to receive the limbus ring and further adapted to selectively place the limbus ring on a limbus annulus, wherein the mounting system is movable in a direction substantially parallel to the optical axis.

25. The system of claim 24 further comprising a limbus ring holding tip adapted to selectively secure the limbus ring during placement of the limbus ring on the limbus annulus.

26. The system of claim 25 wherein the limbus ring holding tip comprises a cylinder edge adapted to selectively engage a top annular groove of the limbus ring.

27. The system of claim 25 wherein the limbus ring holding tip comprises a retaining groove that is substantially complementary to the curvature of the limbus ring, and further comprising an adhesive surface disposed on a contact edge of the retaining groove for retaining the limbus ring.

28. A method of adjusting vision in an eye, comprising mounting a ring as in claim 1 to a limbus annulus of the eye.

* * * * *